United States Patent
Cully et al.

(10) Patent No.: US 10,080,643 B2
(45) Date of Patent: Sep. 25, 2018

(54) STENTED VASCULAR GRAFT

(71) Applicant: W. L. Gore & Associates, Inc., Newark, DE (US)

(72) Inventors: Edward H. Cully, Flagstaff, AZ (US); Deenu Kanjickal, Flagstaff, AZ (US); Bret J. Kilgrow, Flagstaff, AZ (US); Larry J. Kovach, Flagstaff, AZ (US); Timothy T. Stringer, Flagstaff, AZ (US)

(73) Assignee: W. L. Gore Associates, Inc., Newark, DE (US)

( * ) Notice: Subject to any disclaimer, the term of this patent is extended or adjusted under 35 U.S.C. 154(b) by 394 days.

(21) Appl. No.: 15/053,822

(22) Filed: Feb. 25, 2016

(65) Prior Publication Data

US 2016/0235518 A1 Aug. 18, 2016

Related U.S. Application Data

(63) Continuation of application No. 14/559,095, filed on Dec. 3, 2014, now Pat. No. 9,295,542, which is a
(Continued)

(51) Int. Cl.
*A61F 2/07* (2013.01)
*A61F 2/97* (2013.01)
(Continued)

(52) U.S. Cl.
CPC .............. *A61F 2/07* (2013.01); *A61F 2/064* (2013.01); *A61F 2/82* (2013.01); *A61F 2/852* (2013.01);
(Continued)

(58) Field of Classification Search
CPC ...... A61F 2/07; A61F 2/86; A61F 2/82; A61F 2/852; A61F 2/064; A61F 2/97;
(Continued)

(56) References Cited

U.S. PATENT DOCUMENTS 3,657,744 A 4/1972 Ersek
4,130,904 A 12/1978 Whalen
(Continued)

FOREIGN PATENT DOCUMENTS

DE 10104806 A1 8/2002
EP 1192906 A1 4/2002
(Continued)

OTHER PUBLICATIONS

Anthanasiou T, Kapetanakis E, Rao C, et al. Axillary artery to left anterior descending coronary artery pypass with an externally stented graft: a technical report. Journal of Cardiothoracic Surgery 2008; 3:6.
(Continued)

*Primary Examiner* — Katherine M Shi
*Assistant Examiner* — Michael Mendoza

(57) ABSTRACT

A vascular graft incorporating a stent into a portion of its length. While various materials may be used for the vascular graft, the graft is preferably an ePTFE graft. The stent is preferably a self-expanding stent, although it may alternatively be a balloon expandable stent. The vascular graft preferably has a continuous inner tubular liner that extends between the opposing ends of the graft and provides a continuous luminal surface for blood contact that is uninterrupted by seams or joints. The length portion of the graft that does not include the stent has a greater wall thickness than does the portion including the stent.

20 Claims, 12 Drawing Sheets

Related U.S. Application Data continuation of application No. 11/854,735, filed on Sep. 13, 2007, now Pat. No. 8,906,081.

(51) Int. Cl.
*A61F 2/852* (2013.01)
*A61F 2/86* (2013.01)
*A61F 2/06* (2013.01)
*A61F 2/95* (2013.01)
*A61F 2/89* (2013.01)
*A61F 2/82* (2013.01)

(52) U.S. Cl.
CPC .................. *A61F 2/86* (2013.01); *A61F 2/97* (2013.01); *A61F 2/06* (2013.01); *A61F 2/89* (2013.01); *A61F 2002/065* (2013.01); *A61F 2002/828* (2013.01); *A61F 2002/9511* (2013.01); *A61F 2002/9522* (2013.01); *A61F 2210/0014* (2013.01); *A61F 2230/0069* (2013.01); *A61F 2240/001* (2013.01); *A61F 2250/0067* (2013.01); *Y10T 29/49885* (2015.01); *Y10T 29/49901* (2015.01)

(58) Field of Classification Search
CPC ........ A61F 2002/9511; A61F 2002/065; A61F 2002/828; A61F 2/89; A61F 2/06; A61F 2002/9522
See application file for complete search history.

(56) References Cited

U.S. PATENT DOCUMENTS

| | | |
|---|---|---|
| 4,214,587 A | 7/1980 | Sakura, Jr. |
| 4,550,447 A | 11/1985 | Seiler, Jr. et al. |
| 4,577,631 A | 3/1986 | Kreamer |
| 4,619,641 A | 10/1986 | Schanzer |
| 4,776,337 A | 10/1988 | Palmaz |
| 4,877,661 A | 10/1989 | House et al. |
| 5,122,154 A | 6/1992 | Rhodes |
| 5,123,917 A | 6/1992 | Lee |
| 5,156,620 A | 10/1992 | Pigott |
| 5,275,622 A | 1/1994 | Lazarus et al. |
| 5,330,490 A | 7/1994 | Wilk et al. |
| 5,358,516 A | 10/1994 | Myers et al. |
| 5,360,443 A | 11/1994 | Barone et al. |
| 5,476,506 A | 12/1995 | Lunn |
| 5,476,589 A | 12/1995 | Bacino |
| 5,522,881 A | 6/1996 | Lentz |
| 5,549,663 A | 8/1996 | Cottone, Jr. |
| 5,575,817 A | 11/1996 | Martin |
| 5,578,072 A | 11/1996 | Barone et al. |
| 5,591,195 A | 1/1997 | Taheri et al. |
| 5,591,226 A | 1/1997 | Trerotola et al. |
| 5,628,982 A | 5/1997 | Myers et al. |
| 5,662,700 A | 9/1997 | Lazarus et al. |
| 5,662,701 A | 9/1997 | Plaia et al. |
| 5,665,117 A | 9/1997 | Rhodes |
| 5,667,523 A | 9/1997 | Bynon et al. |
| 5,683,448 A | 11/1997 | Cragg |
| 5,728,131 A | 3/1998 | Frantzen et al. |
| 5,747,128 A | 5/1998 | Campbell et al. |
| 5,755,769 A | 5/1998 | Richard et al. |
| 5,755,774 A | 5/1998 | Pinchuk |
| 5,755,775 A | 5/1998 | Trerotola et al. |
| 5,755,778 A | 5/1998 | Kleshinski |
| 5,800,506 A | 9/1998 | Perouse |
| 5,800,522 A | 9/1998 | Campbell et al. |
| 5,814,405 A | 9/1998 | Branca et al. |
| 5,824,043 A | 10/1998 | Cottone, Jr. |
| 5,843,164 A | 12/1998 | Frantzen et al. |
| 5,855,598 A | 1/1999 | Pinchuk |
| 5,906,641 A | 5/1999 | Thompson et al. |
| 5,984,955 A | 11/1999 | Wisselink |
| 5,993,481 A | 11/1999 | Marcade et al. |
| 6,004,348 A | 12/1999 | Banas et al. |
| 6,019,788 A | 2/2000 | Butters et al. |
| 6,036,723 A | 3/2000 | Anidjar et al. |
| 6,162,246 A | 12/2000 | Barone |
| 6,165,212 A | 12/2000 | Dereume et al. |
| 6,168,619 B1 | 1/2001 | Dinh et al. |
| 6,168,623 B1 | 1/2001 | Fogarty et al. |
| 6,179,849 B1 | 1/2001 | Yencho et al. |
| 6,187,054 B1 | 2/2001 | Colone et al. |
| 6,224,627 B1 | 5/2001 | Armstrong et al. |
| 6,254,632 B1 | 7/2001 | Wu et al. |
| 6,287,335 B1 | 9/2001 | Drasler et al. |
| 6,290,731 B1 | 9/2001 | Solovey et al. |
| 6,315,791 B1 | 11/2001 | Gingras et al. |
| 6,325,820 B1 | 12/2001 | Khosravi et al. |
| 6,344,056 B1 | 2/2002 | Dehdashtian |
| 6,383,214 B1 | 5/2002 | Banas et al. |
| 6,428,565 B1 | 8/2002 | Wisselink |
| 6,443,981 B1 | 9/2002 | Colone et al. |
| 6,468,300 B1 | 10/2002 | Freidberg |
| 6,517,571 B1 | 2/2003 | Brauker et al. |
| 6,575,994 B1 | 6/2003 | Marin et al. |
| 6,605,119 B1 | 8/2003 | Colone et al. |
| 6,629,350 B2 | 10/2003 | Motsenbocker |
| 6,652,570 B2 | 11/2003 | Smith et al. |
| 6,673,102 B1 | 1/2004 | Vonesh et al. |
| 6,709,455 B1 | 3/2004 | Chouinard |
| 6,770,087 B2 | 8/2004 | Layne et al. |
| 6,773,453 B2 | 8/2004 | Ravenscroft |
| 6,790,225 B1 | 9/2004 | Shannon et al. |
| 6,827,731 B2 | 12/2004 | Armstrong et al. |
| 6,849,088 B2 | 2/2005 | Dehdashtian et al. |
| 6,911,040 B2 | 6/2005 | Johnson et al. |
| 6,966,887 B1 | 11/2005 | Chin |
| 7,056,336 B2 | 6/2006 | Armstrong et al. |
| 7,081,129 B2 | 7/2006 | Chobotov |
| 7,147,659 B2 | 12/2006 | Jones |
| 7,147,660 B2 | 12/2006 | Chobotov et al. |
| RE40,122 E | 2/2008 | Thompson |
| 7,578,828 B2 | 8/2009 | Gittings et al. |
| 7,722,665 B2 | 5/2010 | Anwar et al. |
| 8,123,797 B2 | 2/2012 | Anwar et al. |
| 8,906,081 B2 | 12/2014 | Cully et al. |
| 9,295,542 B2 | 3/2016 | Cully et al. |
| 2001/0023369 A1 | 9/2001 | Chobotov |
| 2002/0095205 A1 | 7/2002 | Edwin et al. |
| 2002/0107560 A1 | 8/2002 | Richter |
| 2003/0065377 A1 | 4/2003 | Davila et al. |
| 2003/0120332 A1 | 6/2003 | Hartley |
| 2003/0130720 A1 | 7/2003 | DePalma et al. |
| 2003/0149471 A1 | 8/2003 | Briana et al. |
| 2004/0073282 A1 | 4/2004 | Stanish |
| 2004/0107004 A1 | 6/2004 | Levine et al. |
| 2005/0004653 A1 | 1/2005 | Gerberding et al. |
| 2005/0165467 A1 | 7/2005 | Hunter et al. |
| 2005/0273155 A1 | 12/2005 | Bahler et al. |
| 2005/0288767 A1 | 12/2005 | Kujawski et al. |
| 2006/0122961 A1 | 6/2006 | Kalia et al. |
| 2006/0149351 A1 | 7/2006 | Smirthwaite et al. |
| 2007/0027526 A1 | 2/2007 | Demetriades et al. |
| 2007/0067014 A1 | 3/2007 | Ke et al. |
| 2007/0142897 A1 | 6/2007 | Consigny et al. |
| 2007/0179598 A1 | 8/2007 | Deurig |
| 2007/0198077 A1 | 8/2007 | Cully et al. |
| 2007/0219620 A1 | 9/2007 | Eells et al. |
| 2007/0219642 A1 | 9/2007 | Richter |
| 2008/0009781 A1 | 1/2008 | Anwar et al. |
| 2008/0027534 A1 | 1/2008 | Edwin et al. |
| 2008/0082157 A1 | 4/2008 | Thomas |
| 2009/0171436 A1 | 7/2009 | Casanova et al. |
| 2010/0191322 A1 | 7/2010 | Anwar et al. |

FOREIGN PATENT DOCUMENTS

| | | |
|---|---|---|
| EP | 1700580 A1 | 9/2006 |
| FR | 2768921 A1 | 4/1999 |
| WO | WO-1984003036 A1 | 1/1984 |
| WO | WO-199521592 A1 | 8/1995 |
| WO | WO-199610967 A1 | 4/1996 |

(56) References Cited

FOREIGN PATENT DOCUMENTS

| WO | WO-1996010375 A1 | 4/1996 |
|---|---|---|
| WO | WO-199733532 A2 | 9/1997 |
| WO | WO-199827894 A1 | 7/1998 |
| WO | WO-2002026281 A1 | 4/2002 |
| WO | WO-03082152 A1 | 10/2003 |
| WO | WO-2005115275 A1 | 12/2005 |
| WO | WO-2007084762 A2 | 7/2007 |
| WO | WO-2007123633 A1 | 11/2007 |

OTHER PUBLICATIONS

Battikh K, Rihani R, Lemahieu JM. Acute stent recoil in the left main coronary artery treated with additional stenting. Journal of Invasive Cardiology Case 2003; 15:39-42.

Blum U, Voshage G, Lammer J, et al. Endoluminal stent grafts for infrarenal abdominal aortic aneurysms. New England Journal of Medicine 1997; 336:13-20.

Cerna M, Kocher M, Dlouhy M, et al. Ferx ella esophageal covered stent. Acta Univ. Palacki. Olomuc., Fac. Med. 2000; 143:79-80.

Coulson AS, Moshimia J, Quarnstrom J. A Combination of the elephant trunk anastomosis technique and vascular clips for dialysis grafts. Surgical Rounds 1999;596-1552.

Coulson AS. "Combination of elephant trunk anastomosis and vascular clips for venous end of dialysis grafts" In Vascular Access for Hemodialysis-VII. Henry ML. W.L. Gore & Associates, Inc. Precept Press 2001 79-96.

Dake MD, Kato N, Mitchell RS et al. Endovascular stent-graft placement for the treatment of acute aortic dissection. New England Journal of Medicine 1999; 340:1546-1552.

Ishihara H, Uchida N, Yamasaki C, et al. Extensive primary repair of the thoracic aorta in Stanford type A acute aortic dissection by means of a synthetic vascular graft with a self-expandable stent. Journal of Thoracic Cardiovascular Surgery 2002; 123: 1035-1040.

Kato M, Ohnishi K, Kaneko M, et al. New graft-implanting method for thoracic aortic aneurysm or dissection with a stented graft. American Heart Association Scientific Sessions No. 68 1996, 94:188-193.

Kwolek C. Endovascular management of renal artery stenosis: Current techniques and results. Perspectives in Vascular Surgery and Endovascular Therapy 2004; 16:261-279.

Marin ML, Veith FJ, Cynamon J, et al. Transfemoral endovascular stented graft treatment of aorto-iliac and femoropopliteal occlusive disease for limb salvage. The American Journal of Surgery 1994;168: 156-162.

Masuda EM, Kistner RL, Eklof B, Lipman RA, et al. Stent-Graft Arteriovenous Fistula: An Endovascular Technique in Hemodialysis Access. J Endovasc Surg 1998; 5:18-23.

Moossavi S, Ross JR. Percutaneous Sutureless Venous Anastomosis. Endovascular Today Feb. 2007; 54-56.

Nageh T, Thomas M. Letter to the Editor: Coronary-artery rupture treated with a polytetrafluoroethylene-coated stent. New England Journal of Medicine 2000; 342: 1022-1924.

Noel AA. Beyond the instructions for use: Pushing the limits of infrarenal device application for abdominal aortic aneurysms. Perspectives in Vascular Surgery and Endovascular Therapy 2006; 18: 19-24.

Ross J. Expanded Polytetrafluoroethylene and Nitinol Stent-Graft for Salvage Treatment of Vascular Access Sites: Initial Experience. Henry ML, ed. Vascular Access for Hemodialysis-IX. Los Angeles, CA: W.L. Gore & Associates, Inc. & Bonus Books, Inc; 2005:23:229-234. Discussion.

Slack MC. The role of stenting on coarctation of the aorta. Progress in Pediatric Cardiology 2001; 14:45-57.

Veith FJ, Gargiulo NJ. Endovascular aortic repair should be the gold standard for ruptured AAAs and all vascular surgeons should be prepared to perform them. Perspectives in Vascular Surgery and Endovascular Therapy 2007; 19:275-282.

Vishnevetsky D, Patel P, Tijerino H, et al. Sirolimus-eluting coronary stent. American Journal of Health-System Pharmacy 2004; 61:449-456.

White R, Kopchock G, Zalewski M, et al. Comparison of the deployment and healing of thin-walled expanded PTFE stented grafts and covered stents. Journal Annals of Vascular Surgery 1996; 10:336-346.

Whittaker DR, Fillinger MF. The engineering of endovascular stent technology: A Review. Vascular and Endovascular Surgery Mar. 2006; 40:85-94.

STENTED VASCULAR GRAFT

CROSS REFERENCE TO RELATED APPLICATION(S)

This application is a continuation of U.S. application Ser. No. 14/559,095, filed Dec. 3, 2014, which is a continuation of U.S. application Ser. No. 11/854,735, filed Sep. 13, 2007 (U.S. Pat. No. 8,906,081, issued Dec. 9, 2014), which are hereby incorporated by reference in their entirety.

FIELD OF THE INVENTION

The present invention relates to the field of vascular grafts incorporating a stent along a portion of the length of the vascular graft.

BACKGROUND OF THE INVENTION

Vascular grafts incorporating a stent component at a location along the length of the graft have been described in the patent literature for some time. Many of these descriptions relate to the use of a stent located at at least one end of a vascular graft for the purpose of securing that end of the vascular graft to the luminal surface of the vasculature into which the graft is desired to be implanted. This is done as an alternative to a sutured anastomosis. Ersek, in 1970, taught a bifurcated vascular graft of Dacron® or Teflon® secured at each of its three ends by a stent component; see U.S. Pat. No. 3,657,744.

Other patents teach the use of separate, space-apart stent components along the length of a vascular graft as an alternative way of making a stent-graft. Rhodes, in U.S. Pat. No. 5,122,154, and Lee, in U.S. Pat. No. 5,123,917 described expandable vascular grafts incorporating ring-shaped balloon expandable stent components at intervals along the length of the graft. Various graft materials are described by these two patents including PTFE (polytetrafluoroethylene), ePTFE (porous expanded polytetrafluoroethylene), polyurethane and Dacron®. Materials cited for the stent component include stainless steel and tantalum.

WO84/03036 describes a stent-graft intended for as an arteriovenous graft for kidney dialysis.

SUMMARY OF THE INVENTION

A stented vascular graft incorporating at least one stent into a portion of its length is described. The at least one stent is preferably located at one end of the stented vascular graft. The stent is preferably a self-expanding stent, although it may alternatively be a balloon expandable stent. Likewise, the stent may be a self-expanding stent that can be further balloon expanded. The stent may provide anchoring and resistance to migration of the stented vascular graft following deployment and implantation. The stented vascular graft is intended to provide for simple and quick anastomosis to a body conduit or to a conventional vascular graft, thereby reducing procedural time.

A stent as described herein is a diametrically expandable tubular framework, typically of metal such as stainless steel or nitinol, that is intended to provide support to a body conduit when implanted by expansion to cause it to contact the luminal surface of the body conduit. It has open spaces between adjacent framework elements of the stent. A conventional vascular graft is defined herein as a tubular conduit capable of conveying blood, without loss of blood through the wall of the vascular graft (unless punctured or otherwise damaged). A stent-graft is a stent provided with a covering of vascular graft material that covers the open spaces between adjacent stent elements.

The stented vascular graft preferably has an inner tubular liner (i.e., a tubular element) that extends continuously in uninterrupted fashion between opposing ends of the graft and is made from polymeric materials typically used for conventional vascular grafts such as polyester or ePTFE; ePTFE is preferred. This continuous inner tubular liner provides a continuous luminal surface for blood contact that is uninterrupted, or substantially uninterrupted, by seams or joints. The liner preferably has a relatively thin wall. The length portion of the graft that does not include the stent preferably has a second, outer layer of conventional vascular graft material (i.e., a second tubular element) coaxially surrounding the inner layer, thus providing a thicker graft wall thickness in the unstented region. The greater graft wall thickness in the unstented region provides the desirable attributes of a conventional vascular graft, including good bending properties with kink resistance, good hoop strength and is readily sutured while providing good suture strength (resistance to tearing out of sutures). Additionally, for hemodialysis applications, the greater wall thickness of the unstented region is anticipated to reduce time to achieve hemostasis following the withdrawal of a dialysis needle from a penetration through the wall of the stented vascular graft.

Preferably this second graft layer is close to or even juxtaposed against one end of the stent component when the stent component is located at one end of the stented vascular graft. When the stent component is located between the ends of the stented vascular graft, separate length segments of the second graft layer are located close to, or even juxtaposed against each of the ends of the stent component.

If desired, layers of reinforcing materials such as ePTFE film may be applied to the external surfaces of either or both the inner and outer graft components and/or over the stent for desired purposes such as to increase hoop strength or to aid in joining components.

Although the stented vascular graft may be used for a variety of arterial and venous applications, it is anticipated to be particularly useful as an arteriovenous graft for vascular access during kidney dialysis. A stented end of the graft is preferably intended to provide the distal, venous anastomosis. By eliminating the conventional sewn anastomosis at the distal end of such dialysis grafts, it is anticipated that the rate of graft failure due to intimal hyperplasia at the outflow anastomosis (a common failure mode of these grafts) will be significantly reduced. Accordingly, the stented end of the stented vascular graft may be referred to herein as the distal end while the opposing, unstented end may be referred to as the proximal end. It is recognized that in some implant applications that this relationship may be reversed.

While it is preferred that the stented vascular graft is provided with a stent located at one end, it is apparent that both ends may be provided with stents. Likewise, one or more stents may be provided at locations between the ends of the graft. The stented vascular graft can be made in a variety of forms including various lengths and inside diameters. It may also be tapered along the length of the device so that the inside diameter is different at the opposing ends. Incorporation of tapered sections along the length of the device may be particularly desirable for some dialysis graft applications. Dialysis grafts are often provided with a smaller inside diameter at the arterial end than at the venous end. A tapered length section may be located closer to either end of the graft, or the taper may exist as a uniform, gradual taper extending between the graft ends.

The unstented portion may also be provided with reinforcing rings or spirals attached to the exterior surface; these exterior reinforcing components may be made so as to be removable by a practitioner. Commercial vascular grafts of this type are available from W. L. Gore & Assoc., Flagstaff Az. 86003; see, for example, product no. SRRT06060080L. The unstented portion may also be provided with interior reinforcing in a manner taught by U.S. Pat. No. 5,747,128 to Campbell et al.

Likewise, particularly for hemodialysis applications, the unstented portion may be provided with a layer of a self-sealing elastomer between inner and outer ePTFE layers in a fashion similar to the vascular graft taught by Schanzer in U.S. Pat. No. 4,619,641. The unstented portion may also be provided with other means of rendering the porous graft material non-porous or less porous if desired, such as by the use of coatings or non-porous or reduced porosity films applied to any portion or surface of either the inner or outer graft component. Coatings may also be applied to fill or substantially fill microscopic void spaces between the opposing graft surfaces.

The device may also be made to be bifurcated or trifurcated, with any combination of the device ends provided with a stent or not. These multiple-ended devices may have particular utility in applications where it is desirable to re-perfuse vessels that have been cut off from their natural blood supply by another procedure. The larger end of the device may be connected to a blood source such as the aorta and the smaller ends may be used to re-perfuse smaller vessels (e.g., renal arteries). Still other applications would allow the device to be used to extend the length of a previously placed conventional vascular graft by inserting the stent end into an end of the previously placed graft.

As with other vascular grafts, the stented vascular graft may be provided with known therapeutic agents (e.g., any of various pharmaceutic agents; anticoagulants such as heparin, etc.). WO02/26281A1 provides a representative list of such agents, although the list is not intended to be limiting as to agents that might be used. These agents may be applied to the abluminal and/or luminal surfaces, and/or may be incorporated into the void space of the porous microstructure of the vascular graft tubing (e.g., ePTFE tubing). The application of the agents may be by any known means (e.g., such as coating) that are suitable for attachment of the desired agent to the stented vascular graft

DETAILED DESCRIPTION OF THE DRAWINGS

Figure 1:
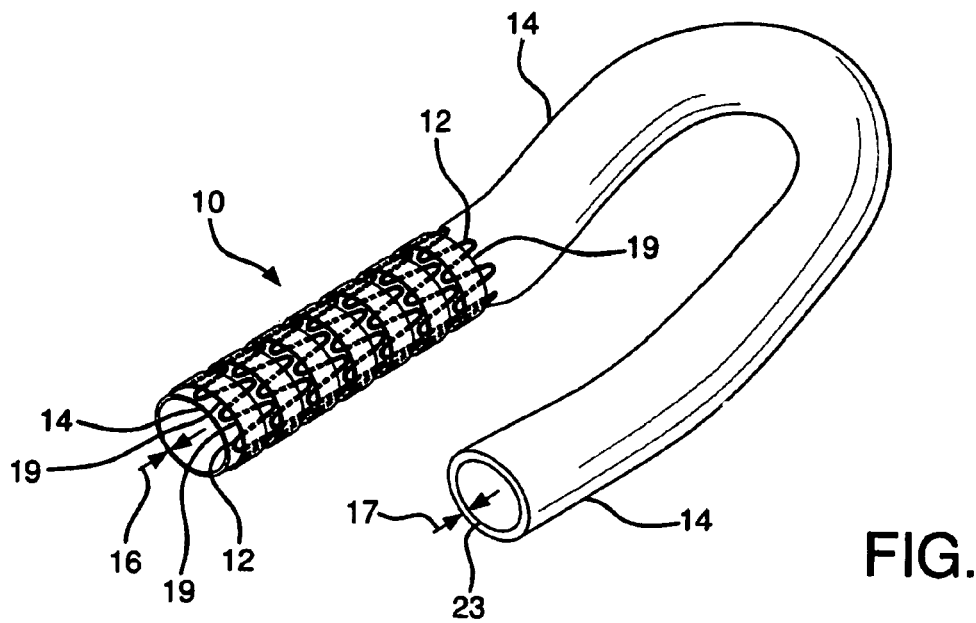
FIG. 1 is a perspective view of the stented vascular graft.

FIG. 1 describes a perspective view of the stented vascular graft 10 wherein, in the embodiment shown, a stent 12 is affixed to one end of a tubular vascular graft 14. The graft 14 in the region of the stent 12 has a wall thickness 16 that is less than the wall thickness of the graft 14 in the unstented region. The wall thickness 17 in the unstented region is at least about 10% thicker than the thickness 16 of the stented region. The unstented region wall thickness 17 may be 20%, or 30%, or 40%, or 50%, or 60%, or 70%, or 80%, or 90%, or 100%, or 150%, or 200%, or 500% or even greater, than the wall thickness 16 of the stented region. It is preferred that the wall thickness 17 of the unstented region be at least about 50% greater than that of the stented region.

Wall thickness may be determined by cutting samples of relatively small surface area (e.g., 1 mm square) and measuring the thickness of those samples with a Mitutoyo model no. 2804-10 snap gauge having a part no. 7300 frame. The measurement is made by placing the graft sample between the measuring pads of the gauge and gently easing the pads into contact with the sample until the pads are in full contact with the sample under the full force of the spring-driven snap gauge. Preferably, the thickness of each respective region of the stent vascular graft should be the result of averaging three samples from different areas of each region. The samples cut from the stented region should be selected from areas that are not covered by a stent element (e.g., a portion of the stent wire) so that any compression of the graft thickness by the stent element is not introduced into the thickness measurement.

Wall thickness of the stented and unstented graft ends is preferably determined by measurements derived from scanning electron photomicrographs (SEM's) of longitudinal cross sections of the different portions of the same stented vascular graft. This is accomplished for ePTFE graft materials by first transversely cutting a length sample of about at least about 2 cm length from the graft (for a graft wherein the stent and adjacent thicker unstented graft are juxtaposed), wherein about half of the length of the sample is composed of the stented portion and the other half of the length of the sample is composed of the unstented portion. The quality of the transverse cuts is not important as long as the wall thickness between the ends of the transverse cuts is not affected. It is apparent that for the stented portion it will be necessary to cut through both the stent material and the tubular graft material.

The sample is submerged in 100% isopropyl alcohol until fully wet out (color of the ePTFE will change from white to a grey, translucent appearance). The sample is then submerged in liquid nitrogen until frozen (at which time the boiling of the liquid nitrogen largely stops). Next, the sample is then cut longitudinally through the wall between the previously cut transverse ends on two sides 180 degrees apart (i.e., two cuts on opposing sides made in a direction parallel to the longitudinal axis of the tubular sample portion) so that the sample is cut in half longitudinally. The quality of these longitudinal cuts is important as any cutting artifacts that might affect wall thickness must be minimal. Any cutting means that minimizes cutting artifacts is suitable, such as surgical scissors. It will again be necessary to cut through both the stent material and the tubular graft material for the stented sample portion.

The resulting half-samples are allowed to warm to ambient and the alcohol is allowed to evaporate from each sample portion. One half-sample is chosen for SEM measurement, sputter-coated as necessary for SEM photography, and placed onto a sample pedestal with cut edges facing up. The sample is placed into the SEM and the cut edges are viewed to look for thickness views with minimal cutting artifacts. Photographic images are made of these appropriate thickness sites with calibrated measurement bars included with each photo. Wall thickness of both the stented portion and the unstented portion is determined from the measurement bars or as indicated by the SEM if the particular machine offers suitable measurement capability.

Stent 12 as shown is a helically wound serpentine wire, secured to the outer surface of tubular vascular graft 14 by a length of tape 19 that is helically wound over the stent 12. Preferably the tape is of a relatively narrow width that covers only the center portion of the width of the serpentine winding, leaving the apices exposed. The stent described is only exemplary; it is apparent that a variety of stent designs may be utilized effectively with the described stented vascular graft.

Figure 2:
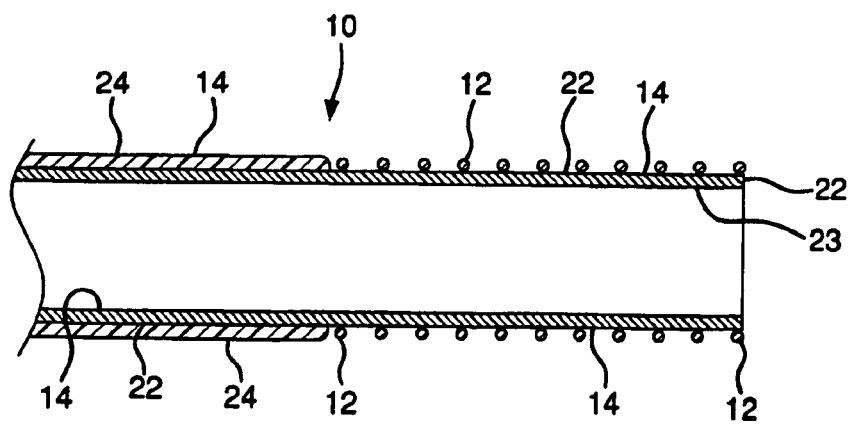
FIG. 2 is a longitudinal cross section of a basic embodiment of the described vascular graft.

FIG. 2 shows a longitudinal cross section of a basic embodiment of the described stented vascular graft 10. This figure describes how in a preferred embodiment the graft is created by the use of an inner tube 22, preferably having a relatively thin wall thickness, that extends for the entire length of the stented vascular graft (i.e., between both opposing ends of the stented vascular graft) including through the stented region. This inner tube 22 may provide the luminal surface 23 (i.e., typically the blood contact surface) for the stented vascular graft. Stent 12 is affixed to a portion of the outer surface of thin tube 22. A second portion of graft tubing 24 is fitted over the unstented region of inner tube 22. One end of this second portion 24 is located close to (i.e., adjacent to) the end of stent 12 that is opposite the distal end of the stent vascular graft. By "close to" is meant within about 2 cm of the end of stent 12. More preferably, this end of the second portion of graft tubing 24 is within about 1 mm of the end of stent 12. It may also abut (i.e., is juxtaposed against) this end of stent 12.

Figure 3:
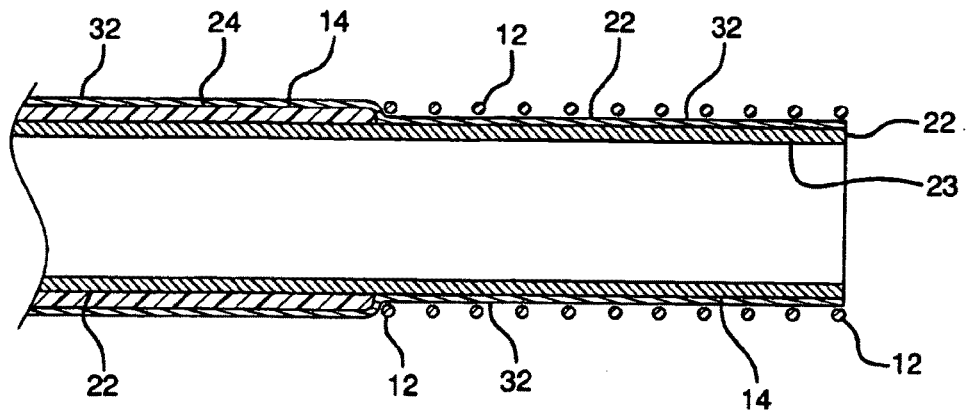
FIG. 3 is a longitudinal cross section of an alternative embodiment of the described vascular graft that adds a layer of external reinforcement.

FIG. 3 is a longitudinal cross section of an alternative embodiment of the described stented vascular graft 10 that adds a layer of external reinforcement 32. For a vascular graft tubing 14 comprised of ePTFE, this reinforcement may be in the form of a helically applied wrap of ePTFE film that provides an increase in hoop strength and in the general integrity of the tubular graft 14.

Figure 4:
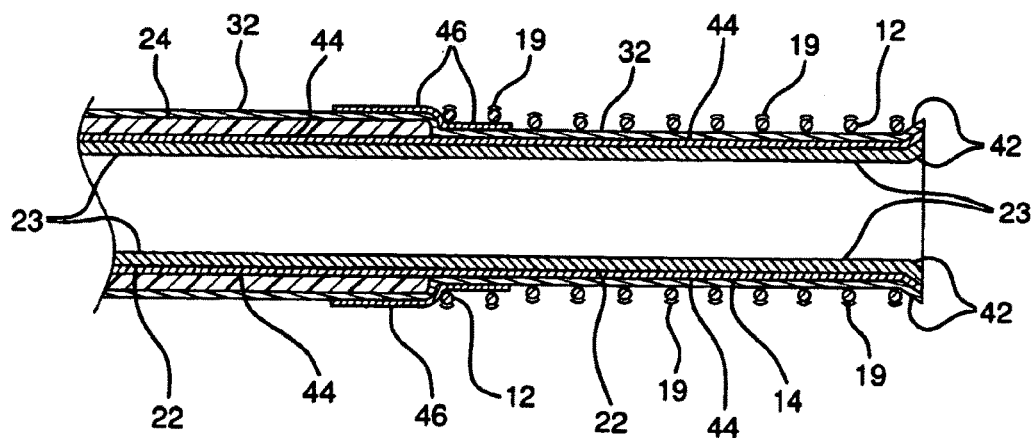
FIG. 4 is a longitudinal cross section of the described vascular graft of FIG. 3 with additional layers of film and further having a flared end at the end of the stent.

FIG. 4 is a longitudinal cross section of the stented vascular graft of FIG. 3 with additional layers of film. Additionally, the vascular graft has a flared end 42 at the common end of the stent 12 and vascular graft 14. As shown, the stented vascular graft 10 is optionally provided with an additional layer 44 of film (e.g., ePTFE film) between inner tube 22 and the second portion of graft tubing 24 (the outer tubing over the unstented section). This additional, optional intermediate layer 44 of film may be used for various purposes depending on the film characteristics. For example, it may be used to provide an impermeable barrier between the inner and outer portions of the stented vascular graft 10. Likewise, it may be used to vary the permeability of the stented vascular graft 10 through its thickness. Layer 44 may also be a material other than film, for example, a layer of elastomer such as a silicone layer to reduce bleeding for hemodialysis graft applications when a dialysis needle is inserted through the graft wall and then withdrawn.

FIG. 4 also describes another optional layer of film 46 that is applied only in the region of the end of the second portion of graft tubing 24 where it terminates against the adjacent end of stent 12. This securing film 46 is used to enhance the integrity of the bond between the end of tubing 24 and the underlying inner tube 22. This figure also schematically shows the length of stent-securing tape 19 that is the preferred method of securing stent 12 to the outer surface of inner tube 22 or to any additional layers of film (e.g., layers 32 and/or 44) that are bonded to the outer surface of inner tube 22. An example of the use of stent-securing tape 19 is shown in greater detail in FIG. 1.

Figure 5:
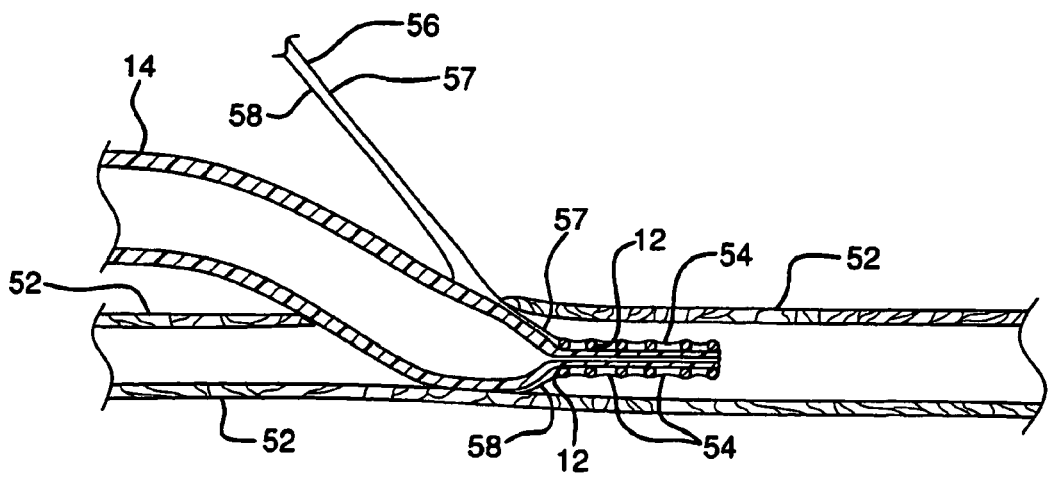
FIG. 5 is a longitudinal cross section of the described vascular graft showing a self expanding stent constrained in a diametrically compacted state as it may be introduced into the vasculature.

FIG. 5 is a longitudinal cross section of the stented vascular graft 10 showing a self expanding stent 12 constrained in a diametrically compacted state as it may be introduced into a body conduit 52 such as the vasculature (e.g., a vein for an arteriovenous graft). Stent 12 is constrained in the compacted state by a constraining sheath 54 that is preferably made of a thin and lubricious material such as ePTFE film. A variety of deployment mechanisms are known in the art of self-expanding stents; the constraining sheath 54 shown is exemplary only. Sheath 54 is preferably removable following deployment of stent 12 within the lumen of a body conduit. Constraining sheath 54 is provided with an extended end 56 which is preferably an extension of the material comprising the constraining sheath 54. Tension may be applied to end 56 to effect deployment of the constrained stent, preferably beginning with the end of the stented vascular graft 10 and progressing back toward the end of the stent 12 that is juxtaposed against the thicker-walled vascular graft portion 24 of the device 10. End edges 57 and 58 converge to form a splittable seam for release of the constraining sheath 54 as will be further described.

Figure 6:
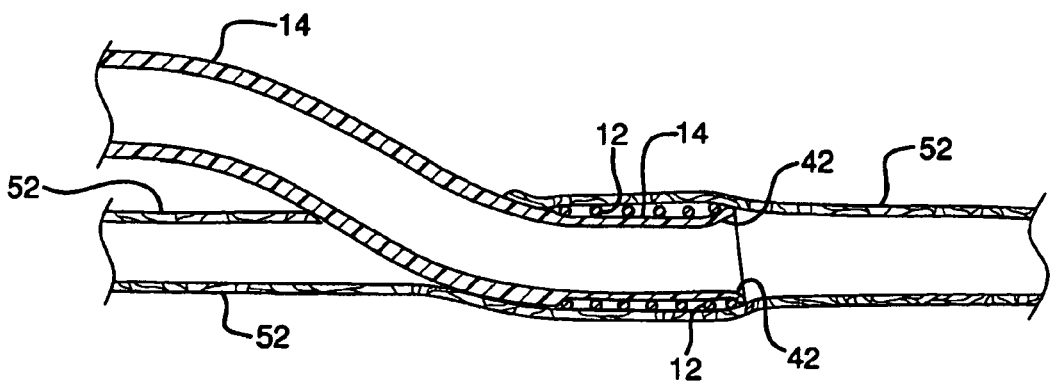
FIG. 6 is a longitudinal cross section showing the vascular graft having the compacted stent as shown in FIG. 5 inserted into and deployed in the vasculature.
Figure 6A:
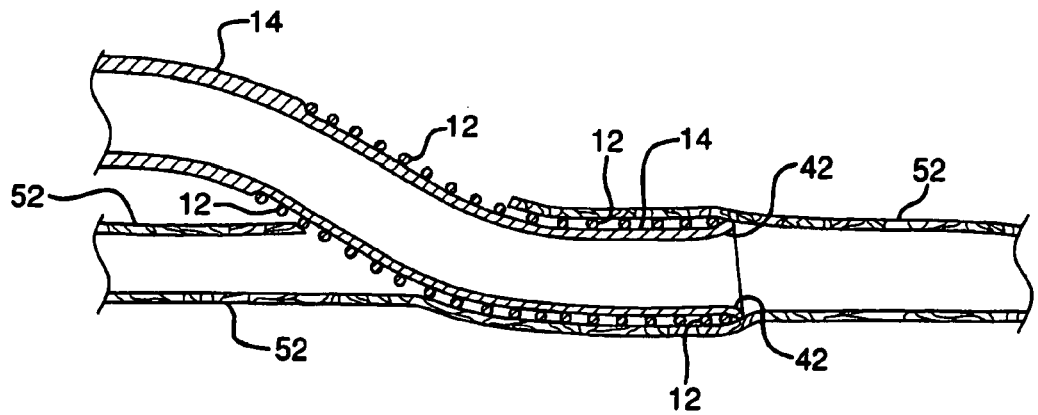
FIG. 6A is an alternative embodiment to that shown in FIG. 6.

FIG. 6 is a longitudinal cross section showing the stented vascular graft 10 following deployment of the compacted stent 12 described previously in FIG. 5. Deployment resulted from the application of tension to end 56 of constraining sheath 54. The tension was provided manually by a practitioner while simultaneously holding device 10 in the desired location with respect to the body conduit 52. Stent 12 is now self-expanded to provide physical contact with the luminal surface of body conduit 52; constraining sheath 54 has been fully removed, also as the result of the applied tension. FIG. 6A describes an alternative to that of FIG. 6 wherein the stented portion extends out of the vein, beyond the venotomy created to insert the stent into the vein.

Figure 7:
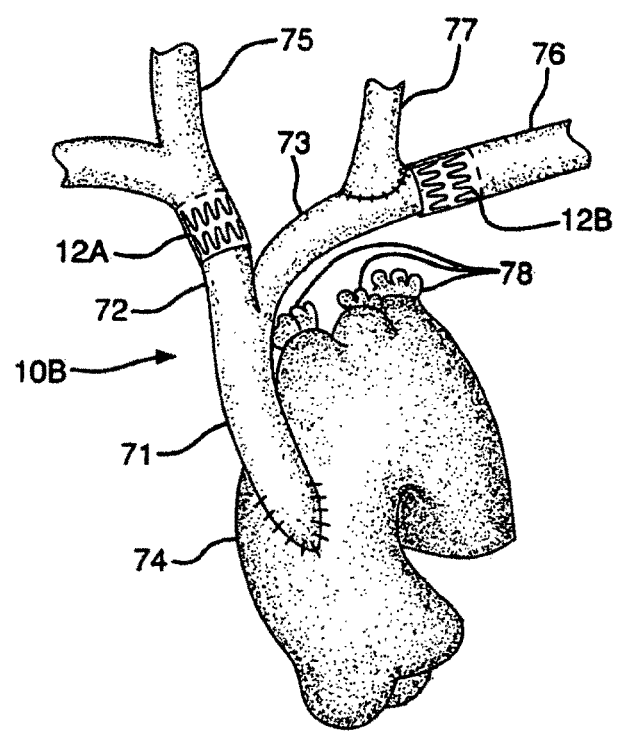
FIGS. 7 and 8 are perspective views showing respectively bifurcated and trifurcated versions of the vascular graft with the stents deployed into the vasculature.

As previously described, the stented vascular graft 10 can be made in a variety of forms including various lengths and inside diameters. It may also be tapered along the length of the device 10 so that the inside diameter is different at the opposing ends. One or both ends of device 10 may be provided with an attached stent. The device may be bifurcated or trifurcated, with any combination of the device ends provided with a stent or not. FIG. 7 is a perspective view of a bifurcated device 10B provided with stents at both of the small diameter ends. The application shown depicts a supra-aortic extra-anatomic bypass based off of the ascending aorta 74 wherein the large diameter trunk 71 of device 10B is conventionally anastomosed to the ascending aorta. Several of the great vessel branches 78 are ligated. Stent 12A is located the end of small diameter leg 72 of device 10B; this end has been inserted and deployed into a transected end of the right common carotid artery 75. Stent 12B is provided at the end of the other small diameter leg 73 of device 10B and has been deployed into a transected end of the subclavian artery 76. The transected end of the left carotid artery 77 is conventionally anastomosed to small diameter 73 of device 10B. The use of such a bifurcated stented vascular graft 10B for a procedure such as depicted by FIG. 7 would be likely to offer a significant reduction in operating time.

Figure 8:
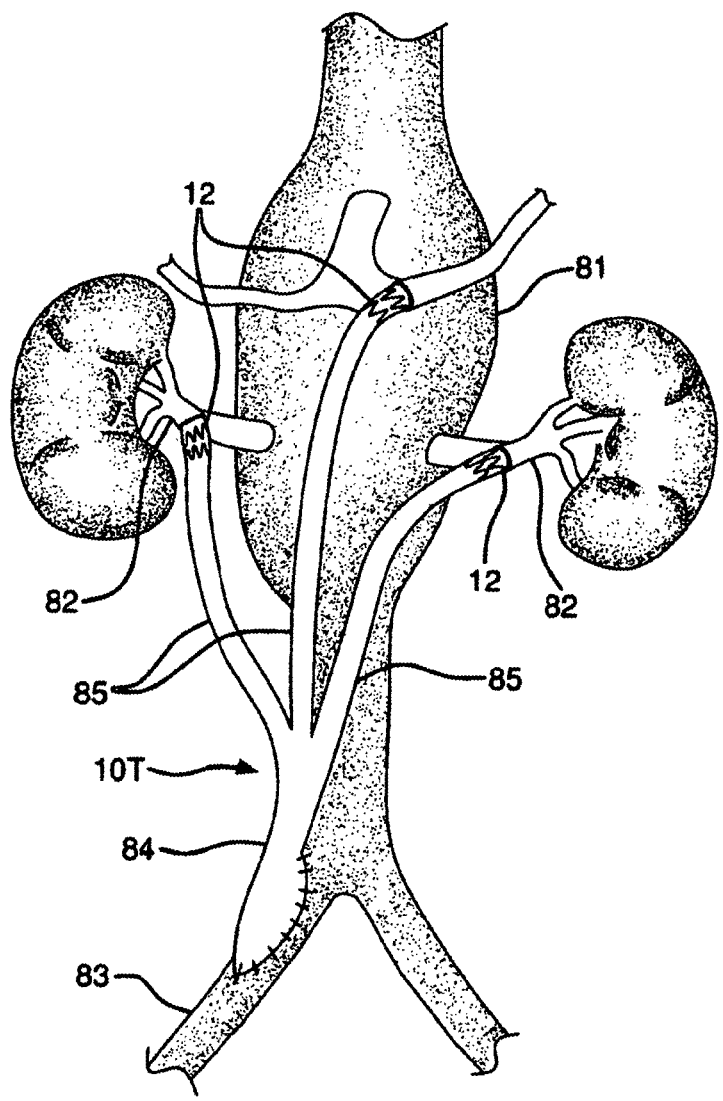

FIG. 8 is a perspective view of a multi-vessel iliac-based anatomic bypass intended to provide kidney perfusion in the case of an aortic aneurysm 81 that has been repaired with an endoluminal stent-graft that results in the renal arteries 82 as well as other arteries (e.g., hepatic) being starved of blood. The end of the large diameter leg 84 of device 10T is sutured to the right iliac artery 83 in conventional fashion, while small diameter legs 85 having stented ends are deployed in the renals and other vessels as necessary. The use of such a trifurcated stented vascular graft 10T for the procedure shown is anticipated to offer a significant saving in operating time in comparison to an equivalent surgery using conventional sutured anastomosis.

Figure 9A:
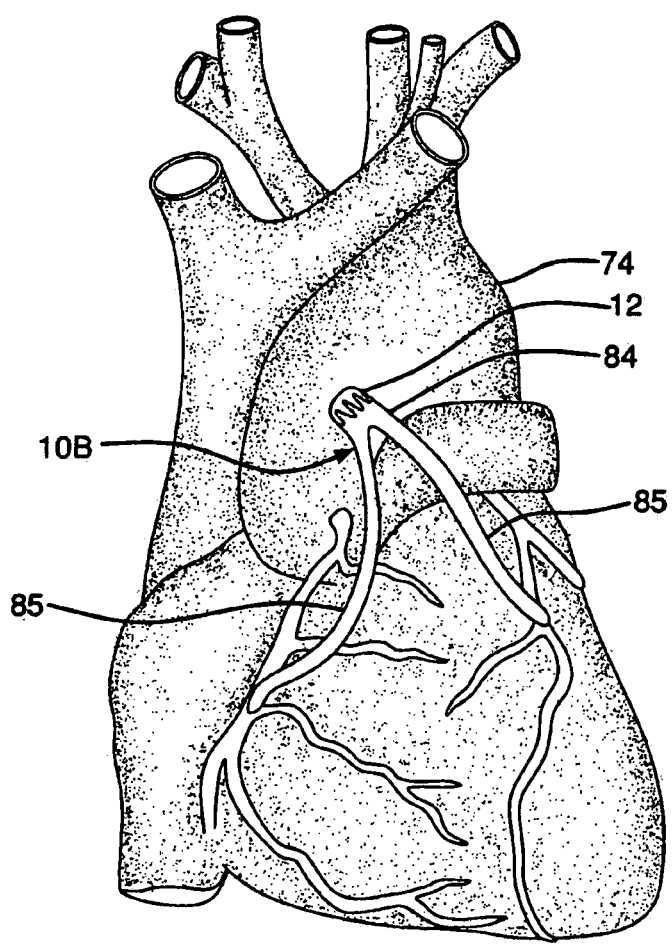
FIGS. 9A and 9B show embodiments useful for cardiac applications.
Figure 9B:
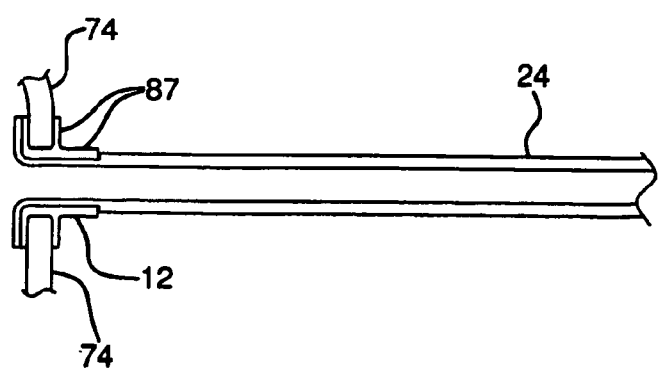

FIG. 9A is a perspective view of a branched embodiment 10B of the stented vascular graft wherein the large end of the device is provided with a stent adapted to be connected through the wall of a vessel such as the ascending aorta 74. It is used in a bypass application to perfuse cardiac vessels that were previously blocked. While the small diameter ends are shown to be conventionally anastomosed to the cardiac arteries, they may alternatively be stented. It is apparent that bifurcated (as shown), trifurcated or devices having even more branches might be used for these cardiac applications. It may be desirable to use a flanged or double flanged stent 87 at the large diameter end of the device 10 as shown in the longitudinal cross section of FIG. 9B.

It is apparent from these descriptions that a variety of branched devices could be constructed for various applications.

An exemplary stented vascular graft according to the description of FIG. 4 was made beginning with a length of ePTFE tubing of 5.8 mm inside diameter and about 0.1 mm wall thickness. This first ePTFE tube had a density of about 0.4 g/cc and a mean fibril length of about 17 microns. The ePTFE tube was fitted over a 6.0 mm diameter stainless steel mandrel, being certain that the tube was extended to its approximate full length after fitting onto the mandrel (thereby ensuring that the length of the tube was not axially compressed). The tube was then helically wrapped with four layers of a 1.9 cm wide tape made from ePTFE film, wrapping from one end of the tube to the opposite end, so that at any transverse cross section of the film-wrapped tube, four layers film thickness were typically present on the outer surface of the ePTFE tube. The film used was a small pore size film of about 2.5 microns thickness made according to U.S. Pat. No. 5,576,589 to Bacino. The film-wrapped tube and mandrel assembly was then placed into a convection oven set at 380° C. for 10 minutes, removed and allowed to cool to ambient.

A second ePTFE tube was obtained, this tube having an inside diameter of 6.0 mm and a wall thickness of 0.7 mm. This tube was diametrically distended by fitting it over a 7.0 mm diameter mandrel, after which it was removed from the mandrel. Before this second tube had time to begin to recover from the brief diametrical distension, it was immediately fitted coaxially over the first, film-wrapped ePTFE tube which remained on the mandrel over which it was first placed. An approximately 15 cm length of the first tube was left exposed (i.e., not covered by the second ePTFE tube) at one end of the first tube. The fitting of the second ePTFE tube over the first was accomplished while ensuring that this second tube was also fully extended longitudinally.

The outer surface of this dual-tube composite was then helically wrapped with four layers of 1.9 cm wide tape made from an ePTFE film, again wrapping from one end of the tubes to the opposite end, with the wrapping extending over the short exposed length of the first tube. This film had a thickness of about 7.5 microns, an approximate mean fibril length of about 50 microns (estimated from scanning electron photomicrographs) and a density of about 0.3 g/cc (for comparison, the density of non-porous PTFE is about 2.2 g/cc).

Next, three layers of a 1.3 cm wide tape made from another ePTFE film were circumferentially wrapped over the end of the second ePTFE tube at the end at which a length of the first tube remained exposed (see FIG. 4, securing film 46). The film used was a low porosity ePTFE film provided with a coating of fluorinated ethylene propylene (FEP) to render it non-porous; the coated film had a thickness of about 2.5 microns. These composite films are made as taught by U.S. Pat. No. 5,358,516 to Myers et al. The center of the width of this film was placed directly over the end edge of the second tube, so that half of the film width was located over the outer surface of the end of the second tube and the other half of the width was covering the adjacent outer surface of the first tube. The opposite end of the second tube (along with the underlying first tube) was secured to the mandrel surface with a metallic clip. The dual-tube composite/mandrel assembly was then placed into a convection oven set at 380° C. for 10 minutes, removed and allowed to cool to ambient.

A stent was provided to be fitted over the exposed length of the first ePTFE tube. While a variety of stent types may be used to create the stented vascular graft, the chosen stent was a helically wound nitinol wire wherein the wire winding included a serpentine pattern incorporating apices pointing alternately to opposite ends of the stent. This type of stent is shown in FIG. 1. The wire was of about 0.15 mm diameter; the amplitude of the serpentine wire pattern (outside wire surface dimension of one apex to an adjacent, opposing direction apex) was about 2.2 mm. The stent included about 26 helical revolutions between the stent ends, extending for a length of about 4.6 cm between the stent ends when fitted over the exposed length of the first ePTFE tube. The end of the stent adjacent the end of the second tube was placed within 1 mm of the end of the second tube, thereby overlying about half of the width of film previously circumferentially wrapped around this location. After aligning the apices of the serpentine wire pattern as shown in FIG. 1, each helical winding of the serpentine wire was wrapped with a 1.0 mm wide tape generally as shown in FIG. 1 to secure the stent to the underlying first ePTFE tube. The film used to make this tape was a low porosity ePTFE film provided with a coating of FEP to render it non-porous; the coated film had a thickness of about 25 microns Additionally, both ends of the stent were circumferentially wrapped with a wider tape made from the same FEP-coated ePTFE film of width sufficient to cover about 7 mm of the length of the stent (about three helical windings of the stent wire). Prior to providing this wrapping at the end of the stent located at the end of the device, a 6 mm outside diameter section of hypotube was inserted into the tip of the stent to provide the flared graft end (per reference no. 42, FIG. 4).

The vascular graft portion of the device (the unstented portion) was axially compressed to about 30% of its length to provide it with rapid recovery generally as taught by U.S. Pat. No. 4,877,661 to House et al. The composite dual tube/stent/mandrel assembly was then placed into a convection oven set at 320° C. for 10 minutes, then removed from the oven and allowed to cool to ambient. This heating process completed the securing of the stent to the underlying ePTFE tubing and was also required as part of the rapid recovery process. After cooling, the assembly was removed from the mandrel.

Finally, following removal of the stented vascular graft assembly from the mandrel, the covering ePTFE film located at the end of the stent at the end of the device, along with any length of the first ePTFE tube extending beyond the stent end, was transversely trimmed off with a scalpel blade at a distance of from 0.1 mm to 0.4 mm from the end of the stent.

Figure 10A:
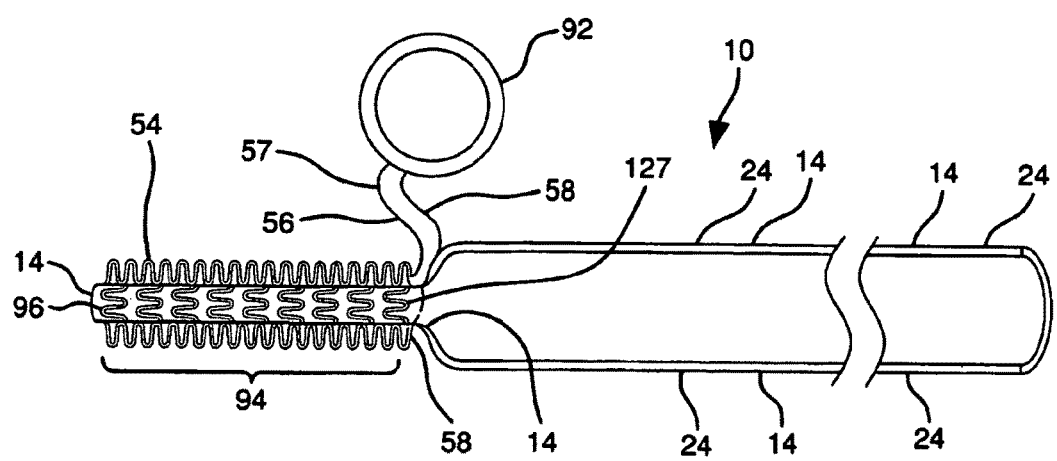
FIGS. 10A-10E show various aspects of a preferred constraining sheath and delivery system.

Stented vascular graft 10 may utilize any suitable form of delivery system that is capable of maintaining the self-expanding stent in a compacted form prior to deployment and provides necessary means for allowing the stent to deploy under the control of a practitioner. Preferably the delivery system is removable from the body conduit into which device 10 has been inserted following stent deployment. These delivery systems can be configured to provide suitable combinations of stiffness and flexibility when tailored for use with a specific stent design to provide for ease of insertion into, for example, a venotomy and to avoid unnecessary bending during the application of tension to the delivery system to initiate deployment. One possible delivery system is described by U.S. Pat. No. 6,224,627 to Armstrong et al. FIG. 10A is a longitudinal cross section of stented vascular graft 10 using a preferred delivery system in the form of an everted, corrugated constraining sheath 54 that constrains self-expanding stent 12 in a compacted state as necessary prior to deployment. The amplitude of the corrugations is exaggerated for visual clarity. The corrugations, oriented circumferentially around the tubular portion 94 of sheath 54, provide increased hoop strength to the sheath 54 and offer better tactile sensitivity to the practitioner during deployment. The use of a greater sheath length resulting from the use of corrugations reduces the required tensile force necessary to cause removal of sheath 54 and deployment of endoprosthesis 12 (due to the length of the corrugated sheath 54 being greater than the length of a similar uncorrugated sheath).

Sheath 54 has a tubular portion 94 and an end 56 portion that extends to a gripping means 92. The tubular portion 94 of constraining sheath 54 is provided having an inner layer and outer, everted layer wherein the outer, everted layer of constraining sheath 54 is everted back over the inner layer at the distal end 96 of stented vascular graft 10, with the result that both ends of the inner and outer, everted layers of the tubular portion 94 of constraining sheath 54 are located where the thicker portion of graft tubing 24 is adjacent the other end 98 of stent 12. End 56 of the outer, everted layer of everted, corrugated constraining sheath 54 extends away from device 10 to a gripping means to which it is affixed such as pull ring 92. The tubular portion 94 of constraining sheath 54 is provided with a splittable seam as will be further described. The edges 57 and 58 of end 56 merge with the tubular portion 94 of constraining sheath 54 at the splittable seam. The application of appropriate tension to end 56 results in splitting of the tubular portion 94 of sheath 54 beginning at the location where end 56 merges with tubular portion 94. Splitting of the outer, everted layer of sheath 54 progresses to the distal end 96 of stent 12 and continues with splitting of the inner layer of sheath 54 which progresses back in the opposite direction. The progression of splitting of the inner layer of tubular portion 94 progressively releases the constraint of self-expanding stent 12, allowing stent 12 to deploy beginning with end 96 and progressing to end 98. This direction is preferred as deployment in the opposite direction risks pushing the stent out of the incision in the vasculature through which it was previously inserted.

Figure 10B:
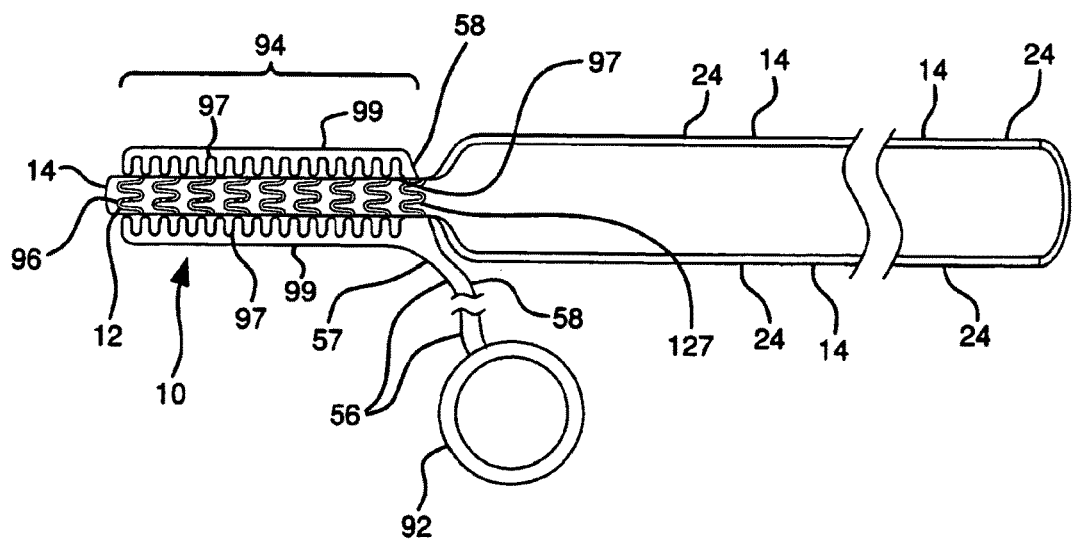

FIG. 10B is a longitudinal cross section of an alternative form of the everted, corrugated constraining sheath 54 wherein the inner layer 97 of the tubular portion 94 is corrugated while the outer, everted layer 99 is not.

Figure 10C:
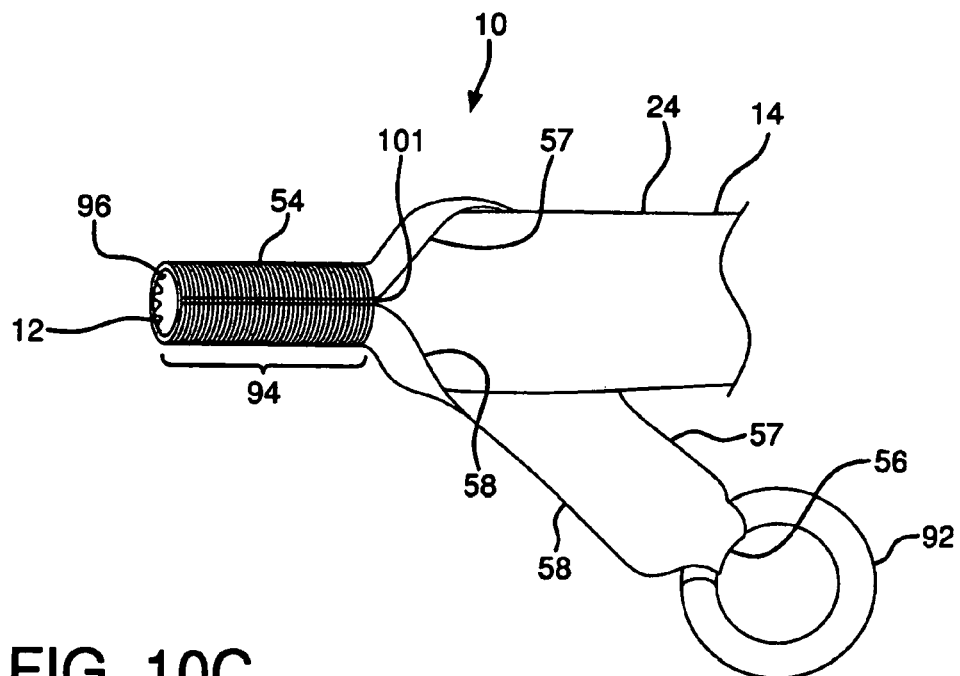

FIG. 10C is a perspective view of the device shown in FIG. 10A. Splittable seam 101 is incorporated into the tubular portion 94 of constraining sheath 54. Splittable seam 101 may be provided by any suitable means of weakening the material of sheath 54 such as by providing a line of perforations made by computer controlled laser cutting. Other means may also be used, including the use of thin materials for sheath 54 that have anisotropic strength properties, offering good hoop strength to the sheath but being inherently splittable along the length of the sheath.

Figure 10D:
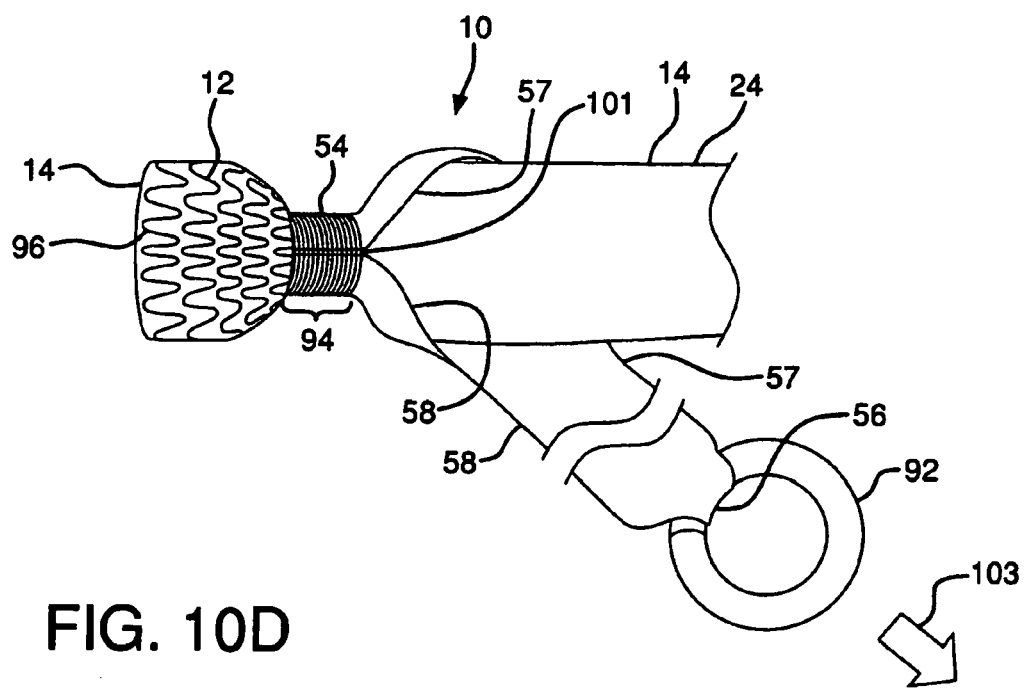

FIG. 10D shows a perspective view of initiation of deployment of stent 12 by the application of tension (shown by arrow 103) to the end 56 of sheath 54 via ring 92. As described briefly above, this tension 103 causes end 56 to become progressively uncorrugated and causes continuing splitting of sheath 54 along splittable seam 101. The outer, everted layer of sheath 54 has been split along splittable seam 101 and withdrawn, and the inner layer of sheath 54 is shown splitting as it also is withdrawn, allowing release and deployment of constrained stent 12. Simultaneously, tension 103 results in withdrawal of sheath 54 from between the deploying stent 12 and the adjacent wall of the body conduit into which it is being deployed.

Figure 10E:
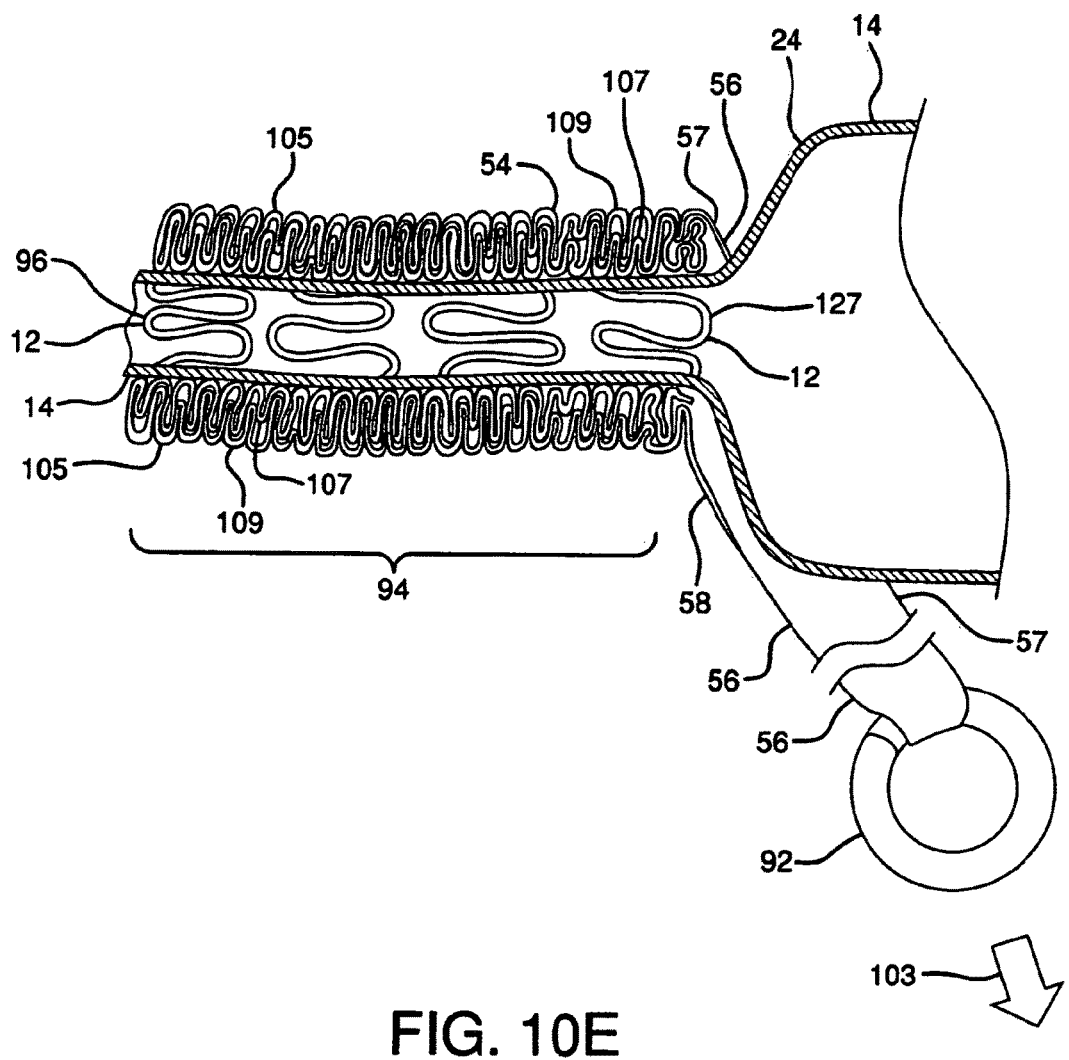

FIG. 10E describes a longitudinal cross section of the stented end of device 10 according to the embodiment described by FIGS. 10A, 10C and 10D. As shown, corrugations 105 may be non-uniform, with the corrugations 105 of the outer, everted layer 109 of sheath 54 not necessarily corresponding exactly to (and consequently not precisely matching) the corrugations 105 of the inner layer 107 of sheath 54.

A preferred tubular material for the partially everted, corrugated constraining sheath 54 is made from a laminated film that is a composite of FEP and ePTFE film wherein the FEP is applied to the ePTFE film as a discontinuous coating that allows the film to remain porous. These composite films are made as taught by U.S. Pat. No. 5,358,516 to Myers et al. A preferred ePTFE film for this laminate is taught by U.S. Pat. No. 5,814,405 to Branca.

To make a 5 cm long, partially everted, corrugated sheath, a 65 cm length of this composite film is paid off onto a slowly rotating stainless steel mandrel, with the 65 cm length parallel to the length of the mandrel. The mandrel is of the diameter desired for the inside diameter of the constraining sheath, the film oriented with the FEP-coated side of the film facing away from the mandrel surface. The film has similar strength properties and tear properties in the length and width directions, so the microstructure of the ePTFE may be oriented with the length of the nodes oriented in a circumferential direction or oriented parallel to the length of the mandrel. Two layers of this film are applied, after which heat from a source such as a soldering iron, adequate to melt FEP, is applied along a line along the length of the resulting film tube. The direction of rotation of the mandrel is reversed, and two additional layers of the film are applied; the reversal of rotation results in the FEP-coated side of the film facing toward the mandrel surface. After the fourth layer is complete, the film is transversely cut with a blade at the end of the mandrel. Finally, a temporary wrap of a tape of helically applied ePTFE film (without FEP-coating) is created over the initial four layers to hold them in place, and the film-covered mandrel is placed into a convection oven set at 320° C. (above the melt temperature of the FEP) for ten minutes. After this time, the mandrel is removed from the oven and allowed to cool to ambient temperature. Following cooling, the temporary overwrap of helically applied ePTFE tape is removed.

A typical resulting film tube has a wall thickness of about 0.020 to 0.025 mm.

Next, the resulting film tube is slid toward one end of mandrel until one end of the film tube extends a short distance (approximately 1 cm) beyond the end of the mandrel. By careful manual manipulation, the end of the tube is everted back over the portion of the tube remaining over the mandrel surface, until 10-12 cm of the end of the tube is everted over the adjacent tube portion. This is repeated for the opposite end of the film tube, resulting in the tube having two layers in the everted region. The tube is then fitted back onto the same mandrel, or optionally, another mandrel of slightly larger diameter to compensate for any diameter increase that resulted from the everting process. The tube and mandrel assembly is then placed into a suitable programmable laser cutting machine (a suitable machine is, for example, a CO$_2$ Laser Marker, model ML-G9320F available from Keyence Corporation, Woodcliff Lake N.J.). The machine may be previously programmed to cut a line of perforations for the full length of the film tube; each individual perforation, for example, being about 0.15 mm wide and of about 0.45 mm length, with adjacent perforations separated by a land of 0.2 mm length.

While still on the mandrel, the sheath is uniformly compressed in an axial direction to create the corrugations. The sheath is axially compressed until its length is 10% of its original, uncompressed length. As shown by FIG. 10E, the everted portion of the tube is corrugated simultaneously with the underlying tube portion. This figure also shows the relative non-uniformity of the corrugations.

Figure 11A:
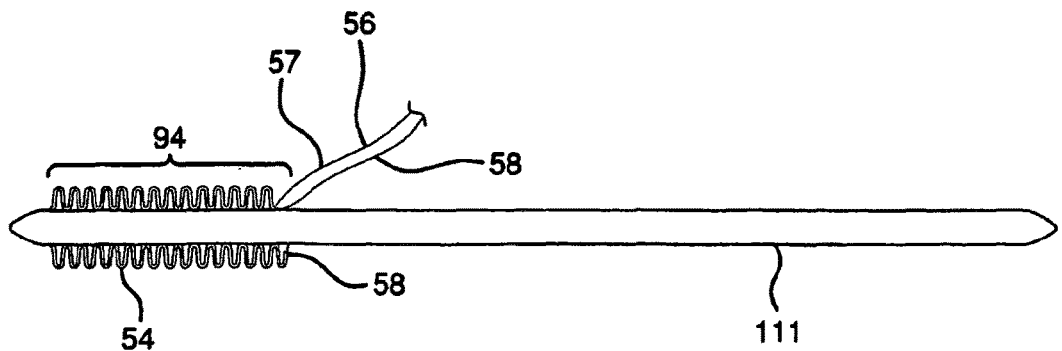
FIGS. 11A-11E show various aspects of the manufacture of the constraining sheath and compacting and loading of the stent portion into the constraining sheath.

FIG. 11A shows a longitudinal cross sectional view of the manufacture of corrugated and everted constraining sheath 54. The tubing from which the sheath 54 is to be made has one end everted back over the inner layer of the tube, creating an outer, everted layer along the length of the tubular portion 94 of sheath 54. The resulting everted tubular portion 94 with inner layer 107 and outer, everted layer 109 (per the relationship described by FIG. 10E) is fitted over a suitable mandrel 111, with the mandrel being a snug fit within the everted tubular portion 94. The opposing ends of the tubular portion 94 are then compressed axially toward each other, causing the corrugations to form along the length of the sheath 54 as shown in FIG. 11A.

Figure 11B:
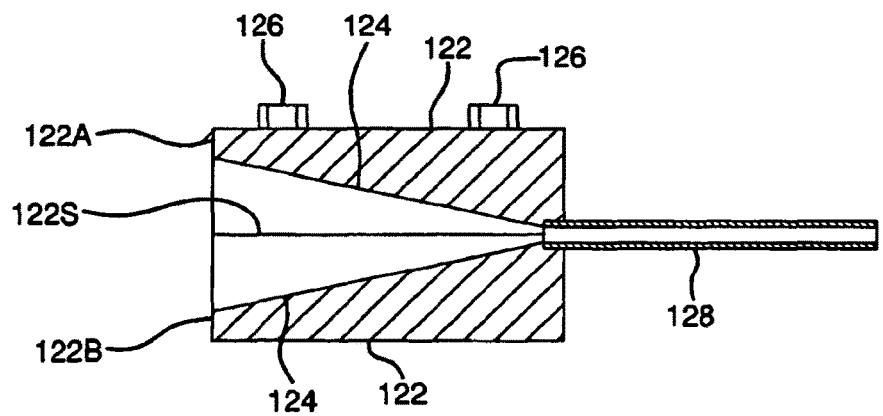

FIG. 11B shows a funnel device 122 useful for compacting a self-expanding stent 12 affixed to one end of stented vascular graft 10 and for inserting the compacted stent 12 into a constraining sheath 54. Funnel device 122 comprises a funnel 124 of a type generally known in the art of manufacturing self-expandable endoprostheses. Other compaction methods may also be used, for example, iris-type compaction devices such as described by U.S. Pat. No. 6,629,350. Funnel device 122 is split along seam line 122S into two halves 122A, 122B that are secured together by suitable means such as fasteners 126. Following compaction and loading of stent 12 into constraining sheath 54, the two halves 122A, 122B of funnel device 122 may be disassembled to remove stented vascular graft 10. Funnel device 122 has a length of thin-wall metal tubing 128 removably attached to funnel device 122 at the small end of funnel 124; the inside diameter of tubing 128 corresponds to the inside diameter of the small end of funnel 124. Tube 128 is aligned to share a common axial centerline (not shown) with funnel 124. A suitable thin-wall tubing is a stainless steel hypotube made by Microgroup, Inc., part no. 304H11XX (Meadway Mass.).

Figure 11C:
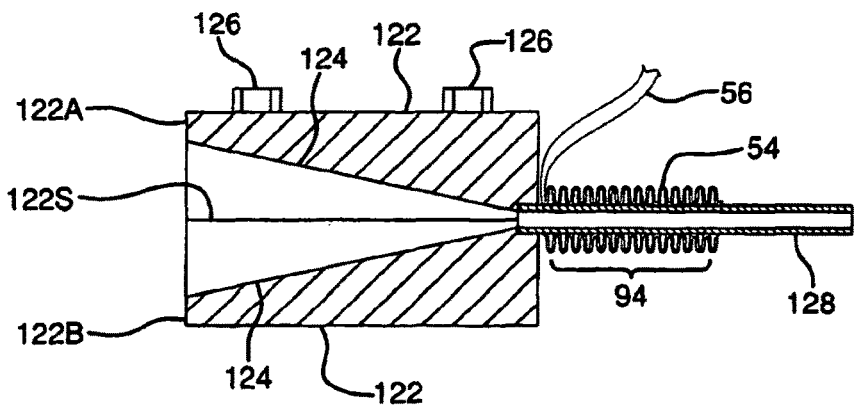
Figure 11D:
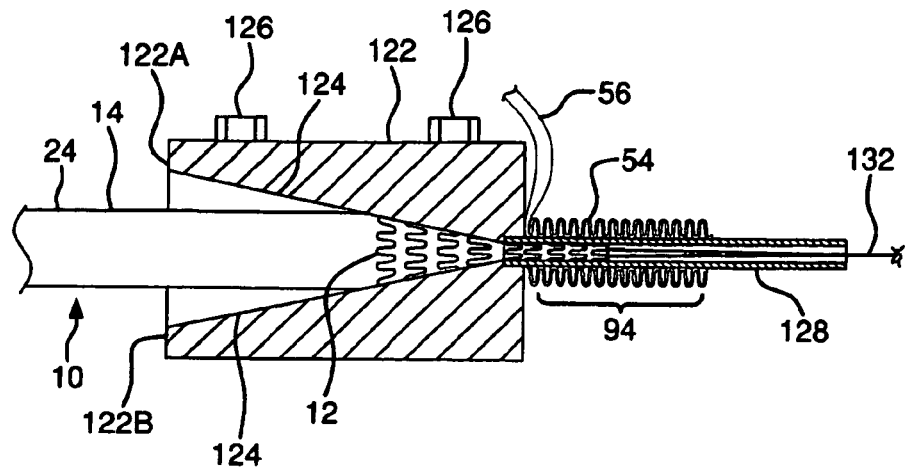
Figure 11E:
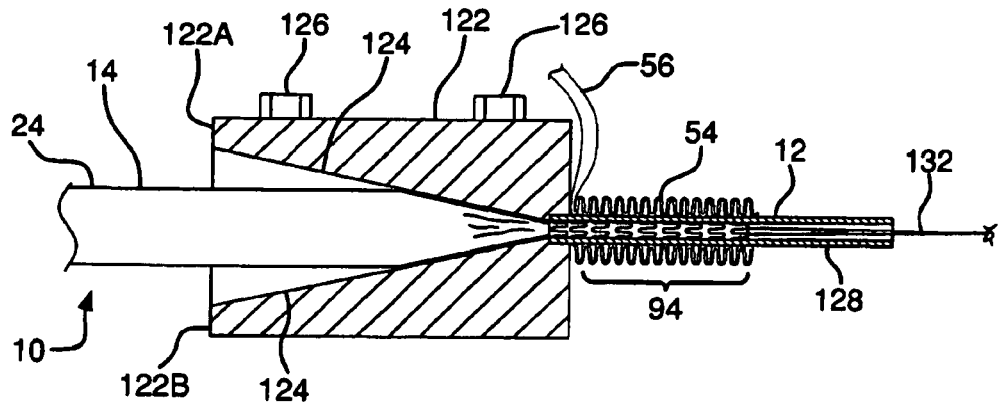

Tubular portion 94 of corrugated and everted sheath 54 is next fitted over the outside of tube 128, as shown by FIG. 11C. This is readily accomplished by sliding tubular portion 94 directly off of mandrel 111 (FIG. 11A) and directly onto the outer surface of tube 128 while one end of mandrel 111 is held abutted against the end of tube 128 that is opposite funnel 124. End 56 of constraining sheath 54 should be located adjacent to the end of funnel 124 as shown. FIG. 11D shows stent 12 being pulled via temporary traction lines 132 into funnel 124 (nitinol stents may require simultaneous chilling with a refrigerant spray) and on into the lumen of tube 128 as stent 12 is compacted. FIG. 11E shows the full length of compacted stent 12 contained within the lumen of tube 128. Following this step, tube 128 is removed from its attachment to funnel 124 by moving it away from the funnel while tubular portion 94 of sheath 54 is held in place around compacted stent 12. With the removal of tube 128, compacted stent 12 is contained within the tubular portion 94 of constraining sheath 54. Finally, the two halves 122A, 122B of funnel device are disassembled and separated, allowing removal of the stented vascular graft 10 with the compacted stent 12 contained within constraining sheath 54.

Another deployment system somewhat similar to the everted, corrugated constraining sheath 54 may be made by using a length of a thin ePTFE tube (e.g., having a wall thickness of about 0.1 mm, density of about 0.4 g/cc and a mean fibril length of about 17 microns) and having a microstructure of fibrils oriented parallel to the length of the tube wherein a portion of the length of the tube has been provided with a coating of a polymer such as a polyimide. Preferably, the coating is impregnated into the void spaces of the outer surface of the porous microstructure of the ePTFE tubing for good adhesion. One means of achieving this is by the use of a suitable amount of a suitable solvent in the coating polymer. The coated ePTFE tube (having a wall thickness of, for example, about 0.18 mm) has excellent hoop strength but may be readily split through the wall by tearing in a direction parallel to the length of the tube. The use of sheath 121 configured as shown allows for deployment beginning at distal end 96 of stent 12 and progressing to proximal end 127 of stent 12.

Figure 12:
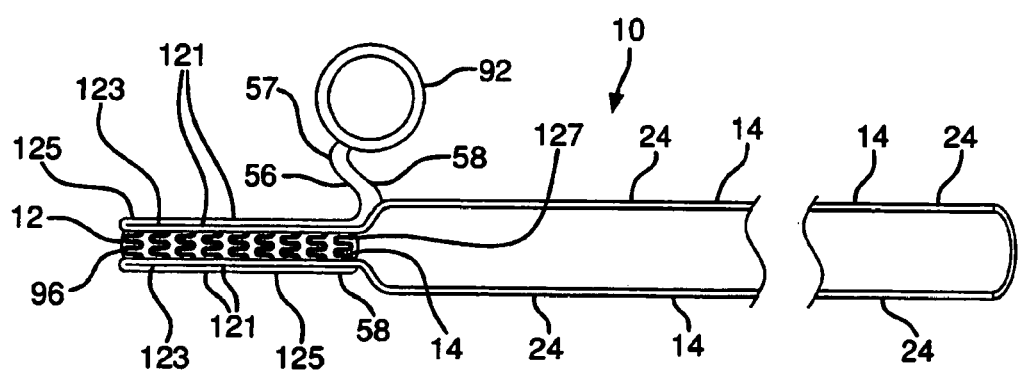
FIG. 12 is a longitudinal cross section of an alternative constraining sheath and delivery system.

FIG. 12 is a longitudinal cross sectional view of this type of deployment system. Sheath 121 is fitted around compacted stent 12 by means such as previously described, such that the portion of sheath 121 surrounding stent 12 everts back over itself at the distal end 96 of stent 12 and accordingly has an inner layer 123 and an outer layer 125. The proximal end of outer layer 125 continues to extended end 56 that is attached to means such as pull ring 92 intended to enable a practitioner to apply tension to sheath 121 to initiate longitudinal splitting and deployment of self-expanding stent 12. Preferably, only inner layer 123 of sheath 121 is provided with the polymer coating while the underlying ePTFE tube extends to pull ring 92. As previously described, extended end 56 is split longitudinally to allow it to diverge from the proximal end 127 of stent 12 as well as providing a starting point for splitting of the tubular length of sheath 121. Inner layer 123 and/or outer layer 125 may additionally be provided with perforations or slots or other means to more easily enable splitting of sheath 121 during deployment.

While particular embodiments of the present invention have been illustrated and described herein, the present invention should not be limited to such illustrations and descriptions. It should be apparent that changes and modifications may be incorporated and embodied as part of the present invention within the scope of the following claims.

We claim:

1. A method of treating a patient, the method comprising:
introducing a stent of an implantable prosthesis into a body conduit of a patient, the implantable prosthesis including a first tubular vascular graft that has a length, an inside diameter and two ends, the length including a first length portion and a second length portion that together make up the entire length of the implantable prosthesis, the second length portion having a greater length than the first length portion, the stent being secured coaxially over the first length portion of the first tubular vascular graft and having a length corresponding to the first length portion, and a second tubular vascular graft wherein the combination of the second tubular graft and the second length portion of the first tubular vascular graft does not coaxially cover the stent; and
deploying the stent of the implantable prosthesis in the body conduit of the patient such that the second tubular vascular graft extends external to the body conduit.

2. The method of claim 1, wherein the stent is self-expanding and is constrained by a constraining member and deploying the stent in the body conduit includes inserting at least a portion of the stent into the body conduit with a delivery device.

3. The method of claim 1, wherein introducing the stent of the implantable prosthesis into the body conduit includes creating an opening in the body conduit and inserting the stent of the implantable device into the body conduit.

4. The method of claim 3, wherein deploying the stent of the implantable prosthesis in the body conduit of the patient includes placing the stent into physical contact with the luminal surface of the body conduit.

5. The method of claim 3, wherein the stent is inserted into the body conduit through the opening such that the entire stent is received in the body conduit.

6. The method of claim 3, wherein the stent is partially inserted into the body conduit through the opening such that a portion of the stent extends out of the body conduit through the opening in the body conduit.

7. The method of claim 1, wherein introducing the stent of the implantable prosthesis into the body conduit includes ligating the body conduit and inserting the stent into the ligated body conduit.

8. The method of claim 1, wherein the stent is introduced into the body conduit while the stent is constrained in a diametrically compacted state by a sheath, and further wherein deploying the stent includes tensioning an end of the sheath to effect deployment of the constrained stent.

9. A method of implanting a prosthesis, the method comprising:
introducing a stent of an implantable prosthesis into a first body conduit of the patient, the implantable prosthesis having a first end, a second end, and an overall length and including a first tubular vascular graft defining a continuous inner lumen extending the overall length of the implantable prosthesis, the overall length including a first portion and a second portion, the second portion having a greater length than the first portion, the stent being coaxially secured about a first portion of the first tubular vascular graft, and a second tubular vascular graft secured about a second portion of the first tubular vascular graft without covering the stent; and
deploying the stent in the first body conduit of the patient to secure the first end of the implantable prosthesis in the first body conduit.

10. The method of claim 9, further comprising suturing the second end of the implantable prosthesis to a second body conduit to form an anastomosis between the first and second body conduits.

11. The method of claim 9, wherein the stent is self-expanding and the stent and the first portion of the first vascular graft are constrained by a constraining member, and further wherein deploying the stent in the first body conduit includes releasing the constraining member to transition the stent and the first portion of the first vascular graft from a constrained configuration having a first diameter to a deployed configuration having a second diameter that is greater than the first diameter.

12. The method of claim 9, wherein the stent is self-expanding and is constrained by a constraining member and deploying the stent in the first body conduit includes inserting the first end of the implantable prosthesis into the first body conduit with a delivery device.

13. The method of claim 12, wherein introducing the stent of the implantable prosthesis into the first body conduit includes creating an opening in the first body conduit and inserting the stent of the implantable prosthesis into the first body conduit.

14. The method of claim 11, wherein the stent is entirely inserted into the first body conduit through the opening.

15. The method of claim 11, wherein the stent is partially inserted into the first body conduit through the opening such that a portion of the stent extends out of the first body conduit through the opening in the first body conduit.

16. The method of claim 9, wherein introducing the stent of the implantable prosthesis into the first body conduit includes ligating the first body conduit and inserting the stent into the open end of the first body conduit.

17. The method of claim 9, wherein the stent is introduced into the first body conduit while the stent is constrained in a diametrically compacted state by a sheath, and further wherein deploying the stent includes tensioning an end of the sheath to effect deployment of the constrained stent.

18. The method of claim 9, wherein the stent is constrained by a sheath including a splittable seam and further wherein deploying the stent includes tensioning the sheath to split the splittable seam to release the constrained stent.

19. A method of treating a patient, the method comprising:
introducing a first stent of an implantable prosthesis into a first body conduit of a patient, the implantable prosthesis including:
a first tubular vascular graft having a length, an inside diameter, a first end, and a second end, the length including first end length portion located at the first end of the first tubular vascular graft, a second end length portion located at the second end of the first tubular vascular graft, and a middle length portion extending between the first and second end length portions, a first stent secured coaxially over the first end length portion of the first tubular vascular graft, a second stent secured coaxially over the second end length portion of the first tubular vascular graft, and a second tubular vascular graft secured over the middle length portion of the first tubular vascular graft while not coaxially covering a substantial portion of the first and second stents with the second tubular vascular graft;

deploying the first stent in the first body conduit; and introducing a second stent of an implantable prosthesis in a second body conduit of a patient; and deploying the second stent in the second body conduit.

20. The method of claim 19, wherein the first and second stents are each constrained by a sheath including a splittable seam and further wherein deploying the first and second stents includes tensioning the respective ends of the sheaths to split the splittable seams to release the first and second stents.

* * * * *